(12) United States Patent
Niizeki et al.

(10) Patent No.: US 10,113,029 B2
(45) Date of Patent: Oct. 30, 2018

(54) SPHERICAL MONODISPERSED POLYESTER RESIN AQUEOUS DISPERSION AND PRODUCTION METHOD THEREOF, AND SPHERICAL MONODISPERSED POLYESTER RESIN PARTICLES AND COSMETIC PRODUCT

(71) Applicant: Miyoshi Oil & Fat Co., Ltd., Tokyo (JP)

(72) Inventors: Koichi Niizeki, Aichi (JP); Masahiro Okuya, Aichi (JP)

(73) Assignee: MIYOSHI OIL & FAT CO., LTD., Tokyo (JP)

( * ) Notice: Subject to any disclaimer, the term of this patent is extended or adjusted under 35 U.S.C. 154(b) by 0 days.

(21) Appl. No.: 15/527,388

(22) PCT Filed: Nov. 20, 2015

(86) PCT No.: PCT/JP2015/082736
§ 371 (c)(1),
(2) Date: May 17, 2017

(87) PCT Pub. No.: WO2016/080530
PCT Pub. Date: May 26, 2016

(65) Prior Publication Data
US 2017/0327637 A1   Nov. 16, 2017

(30) Foreign Application Priority Data

Nov. 21, 2014 (JP) ................... 2014-236867

(51) Int. Cl.
| | |
|---|---|
| *C08F 16/06* | (2006.01) |
| *C08G 63/78* | (2006.01) |
| *A61Q 1/00* | (2006.01) |
| *A61Q 19/00* | (2006.01) |
| *A61K 8/85* | (2006.01) |
| *C08J 3/03* | (2006.01) |
| *C08L 29/04* | (2006.01) |
| *C08L 67/00* | (2006.01) |
| *C08L 101/02* | (2006.01) |
| *C08F 20/18* | (2006.01) |
| *C08F 22/02* | (2006.01) |
| *H01J 37/26* | (2006.01) |

(52) U.S. Cl.
CPC ............ *C08G 63/78* (2013.01); *A61K 8/85* (2013.01); *A61Q 1/00* (2013.01); *A61Q 19/00* (2013.01); *C08F 16/06* (2013.01); *C08F 20/18* (2013.01); *C08F 22/02* (2013.01); *C08J 3/03* (2013.01); *C08L 29/04* (2013.01); *C08L 67/00* (2013.01); *C08L 101/02* (2013.01); *H01J 37/26* (2013.01)

(58) Field of Classification Search
USPC .................................. 528/271, 272
See application file for complete search history.

(56) References Cited

FOREIGN PATENT DOCUMENTS

| | | | |
|---|---|---|---|
| JP | 7-69856 | 3/1995 | |
| JP | 7-82385 | 3/1995 | |
| JP | 07069856 | * 3/1995 | ............ G06F 11/28 |
| JP | 7-179534 | 7/1995 | |
| JP | 2001-11294 | 1/2001 | |

OTHER PUBLICATIONS

JP 07069856 Voneda Shigeru et al., abstract Mar. 14, 1995 Abstract.*
International Search Report (ISR) dated Feb. 16, 2016 in International (PCT) Application No. PCT/JP2015/082736.

* cited by examiner

*Primary Examiner* — Terressa Boykin
(74) *Attorney, Agent, or Firm* — Wenderoth, Lind & Ponack, L.L.P.

(57) ABSTRACT

The present invention provides spherical monodispersed polyester resin particles and an aqueous dispersion thereof in an easy and inexpensive way, and a cosmetic product having fine extensibility, which has fine water resistance and smooth touch, and does not provide uncomfortable feeling to the skin.

11 Claims, 3 Drawing Sheets

SPHERICAL MONODISPERSED POLYESTER RESIN AQUEOUS DISPERSION AND PRODUCTION METHOD THEREOF, AND SPHERICAL MONODISPERSED POLYESTER RESIN PARTICLES AND COSMETIC PRODUCT

TECHNICAL FIELD

The present invention relates to a polyester resin aqueous dispersion having a high sphericity and monodispersity, and a method for producing the dispersion, and spherical monodispersed polyester resin particles having fluidity and water resistance, and a cosmetic product using the spherical monodispersed polyester resin particles.

BACKGROUND ART

Various polymer microparticles are used as various spacers used in liquid crystals and the like, antiblocking agents for resin films, fillers for chromatography, ion exchange resins, plastic modifiers, and fluidity/smoothness improving agents for various powder bodies, and are widely used in various fields of pharmaceutical products, cosmetic products, foods and the like. Furthermore, in either of these uses, it is widely known that monodispersed resin particles exert excellent performances.

For example, in solid powder cosmetic products such as makeup cosmetic products, products that are excellent in moldability and impact resistance, are excellent in tight-adhesibility, and have fine extensibility that gives smooth touch but does not give uncomfortable feeling to the skin are demanded. As a method for improving these disadvantages, for the purpose of improvement of fluidity, lubricity and the like, use of various globular resin powders derived from petroleum such as globular polyethylenes, polystyrenes, nylons, polyurethanes and polyacrylics has been proposed (Patent Literature 1). However, these resin powders have problems in corresponding to environments and applying to humans. Therefore, in recent years, polyester-based resin particles derived from plants, such as polylactate, gain attention from the viewpoints of corresponding to environments, affinity to the skin, and the like.

As methods for producing polymer microparticles, in vinyl-based polymers, production of monodispersed min particles has been tried by adding various devises to polymerization methods such as an emulsification polymerization method, a suspension polymerization method, a seed polymerization method and a dispersion polymerization method (Patent Literatures 2 to 4). On the other hand, in polyester-based resins, the polymerization methods thereof are originally different from the above-mentioned polymerization methods.

In the production of polyester-based resin particles, for example, a method including shattering a polylactic acid-based resin in the form of pellets, chips, a bulk or the like by an air jet mill, and a method including shattering at a low temperature by a disc mill at a quite low temperature of liquid nitrogen (hereinafter referred to as a frost shattering method) have been proposed (Patent Literatures 5 and 6). However, the frost shattering method requires equipment for cooling, shattering, classification and the like, and the polylactic acid powder obtained by the shattering method is not globular particles.

Furthermore, a method for obtaining monodispersed resin particles including heat melting, kneading under dispersing, and cooling a resin together with a dispersion medium such as a polyalkylene oxide, a polyalkylenecarboxylic acid or the like in an extrusion molding machine, and dissolving the dispersion medium with a developing solvent such as water (hereinafter referred to as an extrusion molding method) (Patent Literatures 7 to 9) is considered. The extrusion molding method has disadvantages such as decrease in molecular weight and coloring by thermal history; and since the extrusion molding method uses the dispersion medium in a large amount, it is difficult to sufficiently remove the dispersion medium from resin particles, and thus the operations for the removal become complex and expensive. The resin particles obtained by the extrusion molding method are approximately globular, but are difficult to be said to be spherical monodispersed resin particles, and the removal of the dispersion medium is generally insufficient, and thus the surfaces of the resin particles become hydrophilic. Therefore, the resin particles were insufficient for satisfying requirements such as "makeup lasting" in the field of cosmetic products such as powder foundations, for which water resistance is required. Therefore, attainment of spherical monodispersed polyester resin particles having high affinity to the skin, and are excellent in water resistance and thus do not require a hydrophobization treatment has been awaited. Furthermore, in the field of cosmetic products, for example, in the case of use as a scrubbing agent, since resin particles obtained by a shattering method or an extrusion molding method are not spherical, monodispersed resin particles, there are problems that entering of the resin particles into pores and friction on the skin are unstable, and thus the washing of smudge, cuticle and the like is insufficient, uncomfortable feeling is provided to the skin, and the skin is scratched, and the like.

Furthermore, a method for obtaining monodispersed resin particles by dissolving a resin in a solvent, allowing the solution to pass through a porous film, and removing the solvent (Patent Literatures 10 and 11) is proposed. Although a resin dispersion having high monodispersity can be obtained, the production method is complex and requires a special apparatus, and further requires much time and great care. Therefore, the resin particles become extremely expensive.

Furthermore, it is proposed to obtain porous oil-absorbable polylactic acid-based resin microparticles for cosmetic products, or spherical polylactic acid-based resin microparticles having smooth surfaces for toners and the like by forming a two-phase separation system by using an ether-based organic solvent, applying a shear force to this system to give an emulsion, and further bringing the emulsion into contact with a poor solvent having a smaller solubility of the polylactic acid-based resin than that of the ether system to give microparticles (Patent Literature 12), but thus method is not practical in easiness, efficiency, costs and the like from the viewpoints of selective combination of the solvents and the operations and the control thereof, and the monodispersity and stability of the obtained microparticles were not practically satisfiable in the microparticles and the aqueous dispersion thereof.

For example, in the conventional technologies relating to resin particles such as polylactic acid-based particles and aqueous dispersions thereof as mentioned above, resin particles that are spherical, are excellent in monodispersity, and can be produced efficiently at low costs, have not been actually attained.

The applicant also proposed to obtain an aqueous dispersion of biodegradable resin particles by using an ionic polymer as a dispersing agent and by means of stirring (Patent Literature 13), but a room for further improvement and enhancement has been left in stably obtaining spherical monodispersed polyester resin particles and an aqueous dispersion thereof.

CITATION LIST

Patent Literature

Patent Literature 1: JP 2003-12461 A
Patent Literature 2: JP 2008-239791 A
Patent Literature 3: JP 2009-235273 A
Patent Literature 4: JP 2008-239935 A
Patent Literature 5: JP 2013-527204 A
Patent Literature 6: JP 2001-288273 A
Patent Literature 7: JP 2002-327066 A
Patent Literature 8: JP 2005-200663 A
Patent Literature 9: JP 2003-73233 A
Patent Literature 10: JP 2009-178698 A
Patent Literature 11: JP 2009-297612 A
Patent Literature 12: PCT/JP 2012/105140
Patent Literature 13: JP 2001-11294 A

SUMMARY OF INVENTION

Technical Problem

The present invention was made in view of the above-mentioned situation, and aims at providing a novel technical means that can solve the conventional problems, and can stably attain useful spherical monodispersed polyester resin particles and an aqueous dispersion of the spherical monodispersed polyester resin particles in an easy and inexpensive way. Furthermore, the present invention aims at providing a cosmetic product having fine extensibility and scrubbing effect, which has fine water resistance and smooth touch, and does not provide uncomfortable feeling to the skin, by utilizing the fluidity and lubricity possessed by the obtained spherical monodispersed polyester resin particles.

Solution to Problem

In order to solve the above problems, according to the present invention, there is provided a spherical monodispersed polyester resin aqueous dispersion, including a polyester resin dispersed in water,
wherein the polyester resin has a particle average particle diameter in the range of from 1 to 1,000 μm, a sphericity in the range of from 1.00 to 1.10 as an average value (aspect ratio) of the long diameter/short diameter of the particles, and a monodispersity as a coefficient of variation from the average particle diameter and a standard deviation of 8% or less,
the dispersion contains, together with the polyester resin,
(A) an anionic polymer compound having an average molecular weight of 5,000,000 or more and 25,000,000 or less, and
(B) a polyvinyl alcohol, as dispersing agents, at a ratio in the range of from 1/10 to 1/99 by mass ratio (A/B), and
the dispersion has a viscosity in the range of from 0.1 to 5 Pa·s.

According to the present invention, there is provided a method for producing the spherical monodispersed polyester resin aqueous dispersion including mixing a polyester resin, and the dispersing agents (A) and (B), or the dispersing agents (A) and (B) and a viscosity controlling agent, with water and an organic solvent, by means of stirring.

Furthermore, the present invention also provides spherical monodispersed polyester resin particles, which are obtained by separating resin particles from the above-mentioned spherical monodispersed polyester resin aqueous dispersion, and washing and drying the resin particles, and a cosmetic product including the spherical monodispersed polyester resin particles.

Advantageous Effects of Invention

The polyester resin aqueous dispersion liquid of the present invention is provided easily, inexpensively and stably, and the polyester resin particles have high sphericity, are monodispersed, and are also excellent in fluidity (slipperiness) and water resistance. Furthermore, the cosmetic product containing the particles has fine water resistance and smooth touch, does not provide uncomfortable feeling to the skin, and is excellent in extensibility and scrubbing effect.

DESCRIPTION OF EMBODIMENTS

Figure 1:
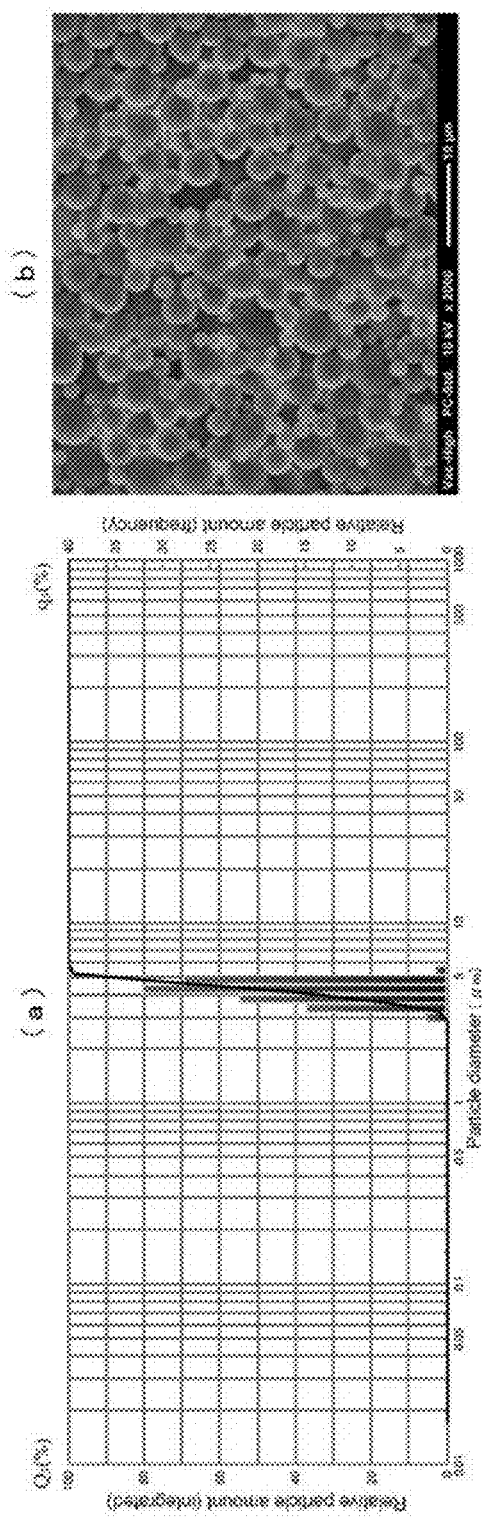
FIG. 1 shows the state of the particles in Example 1, wherein (a) is a measurement chart by a laser diffraction type particle size distribution measurement apparatus, and (b) is an electron microscope photograph.

In the present invention, the polyester resin may be various polyester resins represented by polyester resins derived from plants and biodegradable polyester resins, and for example, typical examples include polylactic acid, copolymers of lactic acid and other hydroxycarboxylic acid, dibasic acid polyesters such as polybutylene succinate, polyethylene succinate and polybutylene adipate, polycaprolactone, copolymers of caprolactone and other hydroxycarboxylic acid, and the like, and these can be used singly, or by mixing two or more kinds.

In the present invention, in order for the polyester resin particles to form a stable water dispersion in which polyester resin particles are stably dispersed in water, as mentioned above, (A) an anionic polymer compound having an average molecular weight of 5,000,000 or more and 25,000,000 or less, and (B) a polyvinyl alcohol, as dispersing agents, at a ratio in the range of from 1/10 to 1/99 by mass ratio (A/B) are contained as dispersing agents.

When the ratio of the anionic polymer compound (A) to the polyvinyl alcohol (B) is less than the above-mentioned range, it becomes difficult to conduct the dispersion, or if the dispersion is conducted, the stability becomes poor. When the ratio is high, the monodispersity and water resistance of the polyester resin particles obtained by using this polyester resin aqueous dispersion liquid may decrease.

The total mass of the above-mentioned dispersing agents (A) and (B) is preferably in the range of from 0.1 to 20% as a mass ratio with respect to the above-mentioned polyester resin. In the case of lower than 0.1%, homogeneous stirring and dispersion become difficult, and thus spherical monodispersed resin particles may not be obtained, whereas when the total mass is more than 20%, the dispersing agent is excessive and thus is not efficient, and the effect on the water resistance is high, and thus the washing in preparing the resin particles becomes complex. Another preferable example of this total mass is in the range of from 1 to 20%.

Furthermore, it is also preferable that the total mass of the above-mentioned dispersing agents (A) and (B) and the polyester resin is in the range of from 1/9 to 7/3 as a mass ratio with respect to the water. When the total mass is lower than 1/9, the polyester resin is at a low content and thus is not efficient, whereas when the total mass is more than 7/3, homogeneous stirring and dispersion may become difficult, or the stability of the aqueous dispersion may become poor.

The anionic polymer compound is an anionic polymer compound having an average molecular weight of 5,000,000 or more and 25,000,000 or less, and polymers or copolymers containing as major component(s) at least one kind of unsaturated carboxylic acid-based monomers, unsaturated sulfonic acid-based monomers and neutralized products thereof are preferably exemplified. That is, homopolymers of monomers such as unsaturated monocarboxylic acid-based monomers, unsaturated dicarboxylic acid-based monomers and unsaturated sulfonic add-based monomers, mutual copolymers of these monomers, copolymers of these monomers such as unsaturated monocarboxylic acid-based monomers, unsaturated dicarboxylic acid-based monomers and unsaturated sulfonic acid-based monomers with other copolymerizable monomer (hereinafter simply referred to as other monomer), and the like are exemplified. The unsaturated monocarboxylic acid-based monomers include acrylic acid, methacrylic acid, crotonic acid, and neutralized products and partial neutralized products of these acids, and the like; the unsaturated dicarboxylic acid-based monomers include maleic acid, fumaric acid, itaconic acid and citraconic acid, and neutralized products and partial neutralized products of these acids, and the like; and the unsaturated sulfonic acid-based monomers include vinylsulfonic acid, allyl sulfonic acid, methacrylsulfonic acid, styrenesulfonic acid, 2-acrylamide-2-methylpropanesulfonic acid, sulfoethyl (meth)acrylate, sulfoethyl maleimide and 3-allyloxy-2-hydroxypropanesulfonic acids and neutralized products and partial neutralized products of these acids, and the like.

In the case when a copolymer of the above-mentioned monomer such as unsaturated monocarboxylic acid-based monomers, unsaturated dicarboxylic acid-based monomers and unsaturated sulfonic acid-based monomers and other monomer is used as the anionic polymer compound, the other monomer is not specifically limited, and examples include amide-based monomer such as (meth)acrylamide, isopropylamide and t-butyl(meth)acrylamide, hydrophobic monomers such as (meth)alkyl acrylate esters, styrene, 2-methylstyrene and vinyl acetate, hydroxyl group-containing monomers such as 2-hydroxyethyl (meth)acrylate, polyethylene glycol mono(meth)acrylate, polypropylene glycol mono(meth)acrylate, allyl alcohol, polyethylene glycol monoallyl ether, polypropylene glycol monoallyl ether, 3-methyl-3-buten-1-ol (isoprenol), polyethylene glycol monoisoprenol ether, polypropylene glycol monoisoprenol ether, 3-methyl-2-buten-1-ol (prenol), polyethylene glycol monoprenol ester, polypropylene glycol monoprenol ester, 2-methyl-3-buten-2-ol (isoprene alcohol), polyethylene glycol monoisoprene alcohol ether, polypropylene glycol monoisoprene alcohol ether, N-methylol(meth)acrylamide, glycerol monoallyl ether and vinyl alcohol, phosphorus-containing monomers such as (meth)acrylamidemethanephosphonic acid, methyl (meth)acrylamidemethanesulfonate ester and 2-(meth)acrylamide-2-methylpropanephosphonic acid, methoxypolyethylene glycol (meth)acrylate, ethoxypropylene glycol (meth)acrylate, and the like can be exemplified.

The anionic polymer compound may also be those cross-linked by dibasic acids such as oxalic acid, malonic acid, succinic acid, glutalic acid, adipic acid, pimellic acid, suberic acid, azelaic acid and sebacic acid, alkyl esters of these dibasic acids, diisocyanates such as hexamethylenediisocyanate glycidyl ether and diphenylmethanediisocyanate, diepoxys such as ethylene glycol diglycidyl ether, polyethylene glycol diglycidyl ether and orthophthalic acid diglycidyl ether, polyglycidyl ethers such as sorbitan polyglycidyl ether and trimethylolpropane polyglycidyl ether, urea, guanidines, dibasic acid dihalides, dialdehydes and the like.

It is considered that the anionic polymer compound is neutralized by preferably a suitable basic compound and used. As the basic compound used for the neutralization, hydroxides of alkali metals, hydroxides of alkaline earth metals, amine compounds such as monoethanolamine and diisopropanolamine, ammonia, and the like are used.

As the anionic polymer compound, an anionic polymer compound having an average molecular weight of 5,000,000 or more and 25,000,000 or less is selected from the above-mentioned ones, and used, and as the specific examples thereof, among the above-mentioned anionic polymer compounds, polymers containing at least one kind of unsaturated monocarboxylic acid-based monomers or neutralized products thereof as major component(s) are preferable, and copolymers of an amide-based monomer and an unsaturated monocarboxylic acid-based monomer or a neutralized product thereof are specifically preferable, and for example, a copolymer of (meth)acrylamide/sodium (meth)acrylate is preferable.

If the average molecular weight is lower than 5,000,000, and more than 25,000,000, it is possible that the monodispersity of the polyester resin particles and the stability of the aqueous dispersion become poor.

As the polyvinyl alcohol (B) that is used together with the anionic polymer compound (A) as above, those having a saponification degree of from 70 to 90% and an average molecular weight of from 50,000 to 300,000 are preferable. If the saponification degree and the average molecular weight are not in these ranges, it is possible that it becomes difficult to maintain a fine dispersed state due to the non-homogeneity flocculation, sedimentation and the like of the resin particles.

The above-mentioned average molecular weights of the anionic polymer compound and the polyvinyl alcohol refer to number average molecular weights. The number average molecular weight can be obtained, for example, by gel permeation chromatography (GPC), by comparing with a standard substance whose molecular weight is already known. Furthermore, the saponification degree of the polyvinyl alcohol can be calculated from the hydroxyl group value of the polyvinyl alcohol.

In the spherical monodispersed polyester resin aqueous dispersion of the present invention, the viscosity thereof is in the range of from 0.1 to 5 Pa·s. At lower than 0.1 Pa·s, and more than 5 Pa·s, the desired object and effect in the present invention are difficult to attain sufficiently.

For example, at lower than 0.1 Pa·s, it is difficult to maintain a fine dispersion state due to phase separation, nonhomogeneity and sedimentation of the resin particles, and the like, and thus strong stirring by using a dispersion apparatus such as a homomixer or a high pressure emulsifier, or the like is necessary. In this strong stirring, since a strong shear force is applied, the molecules of the dispersing agent adsorbed on the dispersed particles are peeled. Consequently, the particle diameter distribution is broadened, and the dispersion itself becomes difficult, and the spherical particles may be broken due to the collision of the resin particles. On the other hand, the viscosity of the solution becomes too high at more than 5 Pa·s, and thus it is possible that fine dispersion cannot be conducted.

In addition, the above-mentioned aqueous dispersion of the present invention may also contain a viscosity controlling agent.

Examples of such viscosity controlling agent include cellulose derivatives such as methyl cellulose, carboxymethyl cellulose, hydroxyethyl cellulose, hydroxyethyl methyl cellulose and hydroxypropylmethyl cellulose, starch derivatives such as cationized starch and etherified starch, plant gums such as gum arabic, guar gum and xanthane gum, animal polymers such as casein, chitosan and chitin, and the like, of which hydroxyethyl cellulose and xanthane gum are preferable.

In the present invention, it is preferably considered that the viscosity controlling agent is used by 0.05 to 0.3% by mass with respect to the polyester resin. When the viscosity controlling agent is lower than 0.05% by mass, the effect thereof is low. On the other hand, in the case of more than 0.3% by mass, stable control of the viscosity of the aqueous dispersion is difficult.

In addition, where necessary, the aqueous dispersion of the present invention can further contain a surface smoothing agent, a water repellent (a hydrophobicity improving agent), a mold release agent, an anticorrosive, a fluidity adjusting agent and the like besides the above-mentioned components, and in order to improve surface smoothness, water repellency, mold release property and the like, waxes such as natural waxes and synthetic waxes can be contained. Examples of the natural waxes include plant-based natural waxes such as candelilla wax, carnauba wax, rice wax, wood wax and jojoba solid wax, animal-based natural waxes such as beeswax, lanolin and whale wax, mineral-based natural waxes such as Montan wax, ozokerite and ceresin, petroleum-based natural waxes such as paraffin wax, microcrystalline wax and petrolatum wax, and the like. Furthermore, examples of the synthetic waxes include synthetic hydrocarbons such as Fischer-Tropsch wax and polyethylene wax, modified waxes such as Montan wax derivatives, paraffin wax derivative and microcrystalline wax derivatives, hydrogenated waxes such as hardened castor oil and hardened castor oil derivatives, 12-hydroxystearic acid, stearic acid amide, anhydrous phthalic acid imide, and the like.

In the aqueous dispersion of the present invention, the average particle diameter of the polyester resin particles is in the range of from 1 to 1,000 μm. Furthermore, the sphericity thereof is in the range of from 1.00 to 1.10 as an average value (aspect ratio) of the long diameter/short diameter of the particles, and the monodispersity thereof is 8% or less as a coefficient of variation from the average particle diameter and a standard deviation.

An aqueous dispersion of such spherical monodispersed polyester resin particles of the present invention can be produced by mixing a polyester resin, and the dispersing agents (A) and (B), or the dispersing agents (A) and (B) and a viscosity controlling agent, with water and an organic solvent, by stirring.

For example, the aqueous dispersion can be obtained by: a pressurization-dispersion method using a sealable container having a stirring apparatus, in which a polyester resin, an anionic polymer compound having an average molecular weight of 5,000,000 or more and 25,000,000 or less and a polyvinyl alcohol, and further a viscosity controlling agent and water as necessary are simultaneously charged, stirred under heating, and pressurized to thereby disperse the polyester resin; a direct dispersion method, in which a molten product containing a polyester resin, an anionic polymer compound and a polyvinyl alcohol, and further containing a viscosity controlling agent as necessary is added to hot water retained under pressurization, and dispersed by stirring; a phase transfer method in which a polyester resin is melted by heat, and an aqueous solution containing an anionic polymer compound and a polyvinyl alcohol, and further containing a viscosity controlling agent as necessary is added to the polyester resin and then stirred to thereby disperse the polyester resin in water; a method in which an organic solvent, water, a polyester resin, an anionic polymer compound, a polyvinyl alcohol, and where necessary, a viscosity controlling agent are added and dispersed by stirring, and the organic solvent is then removed; a method in which an aqueous solution containing an anionic polymer compound and a polyvinyl alcohol, and further containing a viscosity controlling agent as necessary is added to a solution of a polyester resin in an organic solvent, and dispersed by stirring, and the organic solvent is then removed; and the like.

Any method other than the above-mentioned methods can also be suitably adopted as long as it is a method by which an aqueous dispersion of a polyester resin can be obtained. However, considering that application to a wide variety of kinds of polyester resins is possible, and the progress of the hydrolysis, for example, a method in which an organic solvent, water, the above-mentioned polyester resin, an anionic polymer compound and a polyvinyl alcohol, and a viscosity controlling agent as necessary are charged in a sealable container having a stirring apparatus, the temperature is raised under stirring, the solid raw materials are dissolved and dispersed, cooled, and the organic solvent is then removed under a reduced pressure, or a method in which an organic solvent and a polyester resin are charged in a sealable container having a stirring apparatus and dissolved by stirring while raising the temperature to give a polyester resin-dissolved solution; water, an anionic polymer compound and a polyvinyl alcohol, and a viscosity controlling agent as necessary are charged in another stirring container and dissolved to give an aqueous solution, the obtained aqueous solution is added to the sealable container; the mixture is dispersed by stirring while raising the temperature to the solution temperature of the resin; the dispersion is cooled; and the organic solvent is removed by removing the organic solvent under a reduced pressure, is preferable.

The organic solvent include formate esters such as methyl formate, ethyl formate, propyl formate and butyl formate, ester-based organic solvents including acetate esters such as methyl acetate, ethyl acetate, propyl acetate and butyl acetate, chlorine-based organic solvents such as chloroform and carbon tetrachloride, aromatic hydrocarbons such as benzene, toluene and xylene, and the like, and ester-based organic solvents, which have fine resin solubility, specifically formate esters and acetate esters, are preferable. The ratio of the organic solvent to the water is used at a ratio of organic solvent:water=from 1:9 to 9:1, preferably a ratio of from 7:3 to 3:7 by mass ratio. At lower than 1:9, the solubility of the resin may be insufficient, whereas at more than 9:1, the solution of the dispersing agent and the viscosity controlling agent may be insufficient, or spherical monodispersed resin particles may not be obtained. Therefore, the range of from 1:9 to 9:1 is considered. In the present invention, it is preferably considered to set the viscosity after the dispersion under heating during mixing and stirring and cooling in the case when the organic solvent is used to the range of from 1.0 to 60 Pa·s. If the viscosity after the cooling is lower than 1.0 Pa·s or more than 60 Pa·s, homogeneous stirring and dispersion may be difficult, or spherical monodispersed resin particles may not be obtained.

In the production of the spherical monodispersed polyester resin aqueous dispersion liquid of the present invention, by using dispersing agents of the anionic polymer compound and the polyvinyl alcohol at a specific ratio, and further using a viscosity controlling agent as necessary, a rotary stirrer having an impeller used for general dispersion and mixing stirring such as a propeller impeller, a paddle impeller, a turbine impeller, an anchor impeller or a ribbon impeller can be used, without using a special apparatus such as a homomixer or a high pressure emulsifying machine as a dispersion stirring apparatus. Furthermore, the stirring and rotation velocity may also be conditions used in general dispersion and mixing. For example, it is preferably considered to use an impeller having a ratio of an impeller diameter ($d_1$) of the impeller to an inner diameter of a stirring container ($d_2$) (impeller ratio: $d_1/d_2$) during the mixing, of from 0.5 to 0.85. Furthermore, it is preferably considered to set the circumference velocity of the impeller to be in the range of from 1 to 8 m/s.

If the circumference velocity of the impeller is more than 8 m/s, an undue shear force is applied, and the molecules of the dispersing agent adsorbed on the dispersion particles may be peeled and thus the dispersion may become difficult.

The spherical monodispersed polyester resin aqueous dispersion of the present invention is provided easily, inexpensively and stably, and the polyester resin particles have high sphericity, are monodispersed and excellent in fluidity (slipperiness). Therefore, by forming composites with products formed of animal and plant materials such as paper, pulp, nonwoven fabrics, woven fabrics and knitted fabrics of animal and plant fibers, and leather products, the water repellency, oil repellency, water resistance, airtightness, surface gloss and the like of these products can be improved. The method for forming a composite includes a method in which an aqueous dispersion of a polyester resin is applied or atomized onto the surface of a product such as a sheet-like substance, a plate-like substance, a nonwoven fabric, a woven fabric, a knitted fabric, a molded article formed of animal and plant materials, or impregnating these products with the aqueous dispersion, and conducting a heat-pressurizing processing by heating rolls, press, molding or the like, and the like. Furthermore, it is also possible to form a composite by adding the aqueous dispersion to a powder, granules, a slurry, a paste or the like of the animal and plant materials used as the production raw materials of these products, or to form a composite with a powder, granules or the like by using the aqueous dispersion as a binder for bonding the powder, granules or the like of other natural materials such as a powder of an inorganic-based mineral such as clay or sand. For example, in the case when the sheet substrate is paper, pulp and a polyester resin can be formed into a composite by adding the aqueous polyester resin dispersion to a pulp slurry and then making paper.

The spherical monodispersed polyester resin particles of the present invention can be obtained by separating resin particles from the above-mentioned spherical monodispersed polyester resin aqueous dispersion, and then washing and drying the resin particles.

The method for separating the resin particles from the above-mentioned spherical monodispersed polyester resin aqueous dispersion is not specifically limited, and may be any method as long as a solid and a liquid can be separated; for example, the separation can be conducted by using separation apparatuses such as a centrifugation sedimentation machine and a pressure-filtration apparatus, singly or in combination. Examples of the centrifugation sedimentation machine include centrifugation sedimentation machines of a long type, a basket type, a screw decanter type and the like. Examples of the pressure-filtration apparatus include gravity force filtration machines such as a centrifugation filtration machine, a pressure-filtration machine, a vacuum filtration machine, and the like. Furthermore, during the separation, where necessary, a sedimentation promoter such as inorganic salts such as sodium sulfate and edible salt, and organic acids such as lactic acid, acetic acid and citric acid may be added to the above-mentioned spherical monodispersed polyester resin aqueous dispersion liquid, and then the separation may be conducted.

In the washing, a water/alcohol mixed solvent is added to the resin particles obtained by the separation by 100 to 200% by mass with respect to the polyester resin (charged), stirring is conducted at 25 to 40° C. for 1 to 2 hours to thereby allow the dispersing agent and the viscosity controlling agent on the surfaces of the resin particles to detach, the above-mentioned sedimentation promoter is further added as necessary, and the resin particles are separated. Examples of the alcohol for the water/alcohol mixed solvent as a washing solvent include methanol, ethanol, butanol, isopropyl alcohol (IPA), normal propyl alcohol, butanol, isobutanol, TBA (tertiary butanol), butanediol, hexanol, ethyl hexanol, benzyl alcohol and the like, and a mixed solvent of methanol, ethanol, IPA or the like with water, which is used in general washing, is preferable.

In the drying, the resin particles obtained by the washing and separation are dried under a reduced pressure or in hot air, preferably under conditions of 30 to 50° C. and 3 to 24 hours, by using, for example, an air drying apparatus, an oscillation drying apparatus or the like. In addition, the washing of the dispersing agent and the viscosity controlling agent out of the surfaces of the resin particles can be judged by, for example, floating the resin particles on a water surface, and visually confirming the sedimentation state of the resin particles.

In the spherical monodispersed polyester resin particles of the present invention, for the reasons that the resin particles are preferably used in many fields, and that modification and improvement of the physical properties, enlargement of the extent of utilization, and expression of a further new effect are expected in the respective uses, the average particle diameter thereof is from 1 to 1,000 μm, preferably 1 to 850 μm as mentioned above. The monodispersity can be indexed by a coefficient of variation obtained from the average particle diameter measured by using a laser diffraction type particle size distribution measurement apparatus and a standard deviation, and the coefficient of variation is 8% or less, preferably 5% or less. Another preferable example of the average particle diameter is from 1 to 50 μm.

The sphericity can be indexed by the ratio of the long diameter and the short diameter of the resin particles measured by image processing and analyzing a photographic image of the resin particles obtained by electron microscope photographing by using a computer or the like, and the average value (aspect ratio) of the long diameter/the short diameter is from 1.00 to 1.10, preferably from 1.00 to 1.05.

Since the polyester resin particles of the present invention have smooth surfaces, have a high sphericity and monodispersity and water repellency, they are extremely useful in various uses in industries, and can be practically used. Specifically, the polyester resin particles can be used as an additive for cosmetic products such as makeup cosmetic products such as a loose powder, a foundation, a face powder, a water face powder, a face powder, a concealer, a grease paint, an eyebrow, a mascara, an eyeliner, an eye shadow, an eye shadow base, a nose shadow, a lipstick, a gloss and a blusher; skincare cosmetic products such as a face-wash, a cleansing, a cold cream, a skin lotion, a skin milk, a beauty essence, a cream, a sunscreen, an after shave lotion, a shaving soap, a shaving oil and a chemical peeling agent; hair care cosmetic products such as a shampoo, a dry shampoo, a conditioner, a rinse, a rinse-in-shampoo, a treatment, a hair tonic, a hair dressing, a hair oil, a pomade and a hair coloring agent; nail care cosmetic products such as a manicure, a base coat and a top coat; amenity cosmetic products such as a perfume, an eau de cologne, a deodorant, a baby powder, a toothpaste, a mouthwash liquid, a lip cream, a body soap, a hand soap and a soap cosmetic product; a spacer for liquid crystal display apparatuses, an additive for toners, a rheology modifier/additive for toners for developing electrophotographs and coatings, a material for powder body coatings, a mechanical property improving agent for molded articles such as automobile materials and architectural materials, a mechanical property improving agent for films, fibers and the like, a raw material for resin-formed articles of rapid prototyping and rapid manufacturing, a material for flush molding, a paste resin for plastic sols, a powder blocking material, a fluidity-smoothness improving agent for powder bodies, a lubricant, a rubber compounding agent, a polisher, a thickening agent, a filtration agent and a filtration aid, a gelling agent, a flocculating agent, an oil absorbing agent, a mold release agent, a slipperiness improving agent for plastic films and sheets, a blocking inhibitor, a gloss controlling agent, a matting agent, a light diffusing agent, a surface high hardness improving agent, a toughness improving agent, a filler for chromatography, an aid for microcapsules, medical materials such as a drug delivery system and a diagnostic drug, a medical diagnostic agent, a preserving agent for flavor materials and agrochemicals, a catalyst and a support thereof for chemical reactions, a gas adsorbing agent, an ion exchanged resin, a sintering material for ceramic processing, standard particles for measurement and analysis, particles for the field of food industry, and the like. The spherical monodispersed polyester resin particles of the present invention are specifically excellent in affinity to the skin, and are excellent as a component for improving fluidity, smoothness and extensibility for use in cosmetic products having fine water repellency. Furthermore, the spherical monodispersed polyester resin particles of the present invention are mildly-irritating and provide low damages to the skin and have stable and fine effects to enter into the pores and to friction the skin, and thus are excellent as a scrubbing agent for use in cosmetic products for removing smudge and cuticle.

The cosmetic product of the present invention contains the above-mentioned spherical monodispersed polyester resin particles. Examples of the cosmetic product of the present invention include makeup cosmetic products, skincare cosmetic products, hair care cosmetic products, nail care cosmetic products, amenity cosmetic products and the like. Among these, solid powder cosmetic products for which products that are excellent in moldability and impact resistance, have fine water resistance, are excellent in adhesion to the skin and the like, are excellent in tight adhesibility, provide smooth touch and have fine extensibility such that uncomfortable feeling is not provided to the skin are required, such as makeup cosmetic products are preferable. The makeup cosmetic products can be obtained, for example, by using generally incorporated base materials such as extender pigments such as talc, mica, sericite, kaolin, silica, calcium carbonate and aluminum oxide; coloring pigments such as inorganic pigments such as titanium oxide, zinc oxide, yellow iron oxide, black iron oxide, red iron oxide (bengala), ultramarine blue, dark blue and chromium hydroxide, and tar pigments and natural pigments; ultraviolet absorbers such as benzophenone derivatives, paraaminobenzoic acid derivatives, paramethoxycinnamic acid derivatives and salicylic acid derivatives; solid and semisolid oily components such as vaseline, lanolin, ceresin, microcrystalline wax, carnauba wax, candelilla wax, higher aliphatic acids and higher alcohols; liquid oily components such as silicone oil, olive oil, jojoba oil, castor oil, squalene, liquid paraffin, ester oil, diglyceride and triglyceride; water-soluble and oil-soluble polymers; surfactants such as nonionic surfactants, anionic surfactants, cationic surfactants and polyether-modified silicones; gelling agents such as dextrin aliphatic acid esters; lubricants such as zinc aliphatic acids; an antiseptic agent, an antioxidant, a thickening agent, a pH controlling agent, a pearl agent, a coating agent, a flavor material, a moisture agent, a blood circulation promoter, a cooling agent, an antiperspirant agent, a bactericide, a skin activating agent, and the like, and for example, by mixing the spherical monodispersed polyester resin particles of the present invention and a powder body phase by means of a blender, adding an oil phase that has been mixed and dissolved in advance to the powder body phase, kneading the mixture with the blender, and shattering and sieving the product as necessary.

Furthermore, the polyester resin particles are preferable for skin care cosmetic products and amenity cosmetic product, which are required to be biodegradable, affect little on environments, and provide an effect of promoting blood circulation and fine usability such that the skin is difficult to be scratched. The skin care cosmetic products and the amenity cosmetic products can be obtained by mixing the above-mentioned spherical monodispersed polyester resin particles with raw materials that are used in general skin care cosmetic products and amenity cosmetic products. Examples of such raw materials include nonionic surfactants, anionic surfactants, cationic surfactants and amphoteric surfactants. Examples of the oil-based solid animal and plant-based raw materials include beeswax, wood wax, cacao oil, higher alcohols, higher saturated aliphatic acids and the like. Examples of the oil-based liquid animal and plant-based raw materials include olive oil, camellia oil, cottonseed oil, castor oil, oleyl alcohols, oleic acid, squalene and the like. Examples of the solid and semisolid mineral-based raw materials include solid paraffin, ceresine, microcrystalline, wax and the like. Examples of the liquid mineral-based raw materials include liquid paraffin, silicone oil and the like. Examples of the synthetic raw materials include synthetic ester oils, synthetic polyether oils and the like. Furthermore, examples of the water-soluble raw materials include glycerin, propylene glycol, polyethylene glycol, sorbitol, 1,3-butylene glycol, sodium alginate, pectin, methyl cellulose, carboxymethyl cellulose sodium, polyvinyl alcohol, ethyl alcohol, isopropanol and the like. These raw materials are mixed in combination, where necessary, after adding an antiseptic agent, an antioxidant, a thickening agent, a pH controlling agent, a pearl agent, a coating agent, a flavor material, a moisture agent, a blood circulation promoter, a cooling agent, an antiperspirant agent, a bactericide, a skin activating agent and the like.

The mixing ratio of the above-mentioned spherical monodispersed polyester resin particles may be suitably adjusted depending on the intended use, and may be generally from 0.1 to 80% by mass, preferably from 0.1 to 60% by mass.

A further detailed explanation will be made with referring to Examples. As a matter of course, the present invention is not limited by the following examples.

EXAMPLES

1. Preparation of Spherical Monodispersed Polyester Resin Aqueous Dispersion

In Examples and Comparative Examples, the polyester resins, dispersing agents and viscosity controlling agents mentioned below were used.

[Polyester Resins]

Polyester resin A: a commercially available polylactic acid resin (crystalline) having a polystyrene-equivalent Mw of 200,000, a melt flow rate (MFR: JIS K7210-1999, temperature: 190° C., load: 2.16 kgf) of 8.0, a tensile break strength of 73 MPa and a melting point of 164° C.

Polyester resin B: a commercially available polylactic acid resin (non-crystalline) having a polystyrene-equivalent Mw of 180,000, a melt flow rate (MFR: JIS K7210-1999, temperature: 190° C., load: 2.16 kgf) of 2.5 and a tensile break strength of 68 MPa Polyester resin C: a commercially available polybutylene succinate resin having a polystyrene-equivalent Mw of 220,000, a melt flow rate (MFR: JIS K7210-1999, temperature: 190° C., load: 2.16 kgf) of 1.5, a tensile break strength of 57 MPa and a melting point of 115° C.

Polyester resin D: a commercially available butanediol-succinic acid/adipic acid/lactic acid tetrapolymer having a polystyrene-equivalent Mw of 160,000, a melt flow rate (MFR: JIS K7210-1999, temperature: 190° C., load: 2.16 kgf) of 4.5, a tensile break strength of 50 MPa and a melting point of 87° C.

[Dispersing Agents]

Dispersing agent (A) (an anionic polymer compound)

Anionic polymer compound A: a polyacrylic acid-acrylamide (80:20 by mass ratio) copolymer (average molecular weight: 18,000,000)

Anionic polymer compound B: a polymethacrylic acid-acrylamide (90:10 by mass ratio) copolymer (average molecular weight: 8,000,000)

Anionic polymer compound C: a polyacrylic acid-metacrylamide (85:15 by mass ratio) copolymer (average molecular weight: 25,000,000)

Anionic polymer compound D: a polyacrylic acid-acrylamide (80:20 by mass ratio) copolymer (average molecular weight: 4,000,000)

Dispersing agent (B) (a polyvinyl alcohol)

Polyvinyl alcohol A: saponification degree: 80%, average molecular weight: 110,000

Polyvinyl alcohol B: saponification degree: 89%, average molecular weight: 240,000

Polyvinyl alcohol C: saponification degree: 73%, average molecular weight: 50,000

[Viscosity Controlling Agents]

Viscosity controlling agent A: xanthane gum (Echogum, DSP Gokyo Food & Chemical Co., Ltd.)

Viscosity controlling agent B: hydroxyethyl cellulose (SW-25F manufactured by Sumitomo Seika Chemicals Co., Ltd.)

Examples 1 to 21 and Comparative Examples 1 to 5

The components were charged in a sealable dispersion container at each of the component ratios shown in Tables 1 to 4, and were heated to 120° C. in the case when polyester resin A was used, or heated to 70° C. in the cases when polyester resins B to D were respectively used, by a dispersing method using a predetermined stirring-dispersion apparatus, and the dispersion was then quenched up to 40° C. Thereafter, ethyl acetate was removed under a reduced pressure to give a polyester resin aqueous dispersion.

[Dispersing Method]

Dispersing method A: Stirring was conducted by a stirring apparatus having an impeller shape having two paddle impellers on the top and bottom, at predetermined impeller ratio and circumference velocity for 1 hour.

Dispersing method B: Stirring was conducted by a stirring apparatus having an impeller shape having one paddle impeller and an anchor impeller, at predetermined impeller ratio and circumference velocity for 1 hour.

Dispersing method C: Stirring was conducted by using a homomixer MARKII manufactured by Primix, at a rotation number of 10,000 r.p.m. for 3 minutes.

Furthermore, the viscosity and stability in the dispersion step during the preparation of the polyester resin aqueous dispersion (after the heating dispersion and cooling during mixing stirring) and the viscosity and stability of the aqueous dispersion (after the removal of ethyl acetate) were measured and evaluated as follows. The results are shown in Tables 1 to 4.

[Viscosity]

In the dispersion step, the viscosity of the aqueous dispersion was measured by using a type B viscometer (TVB-10M, manufactured by Toki Sangyo Co., Ltd.). The conditions for the measurement were suitably selected from rotors Nos. M1 to M4, and rotation numbers 6, 12, 30 and 60 rpm depending on each viscosity, and the viscosity at 25° C. was measured.

[Stability]

In the dispersion step, the stability of the aqueous dispersion was visually evaluated by the following criteria.

Evaluation Criteria

⊙: No flocculation or sedimentation was observed.

○: When stirring was stopped, flocculation or sedimentation was partially generated.

Δ: Slight flocculation or sedimentation was observed.

x: Separation or flocculation was generated.

2. Method for Preparing Spherical Monodispersed Polyester Resin Particles

In order to prepare polyester resin particles from the obtained aqueous dispersion, a suitable amount of sodium sulfate was added to an aqueous resin dispersion liquid, and the liquid was subjected to vacuum filtration to give a cake-like substance, and a mixed solvent of ion exchanged water/alcohol was added to the cake-like substance by 100% by mass with respect to the polyester resin (charged), stirring was conducted at 25° C. for 1 hour to thereby detach the dispersing agent and the viscosity controlling agent from the surfaces of the resin particles, and washing operations for separating the resin particles by filtering were conducted twice. The resin particles separated by the filtration were dried at 40° C. for 6 hours by using an airflow drier to give polyester resin particles.

Furthermore, the particle states (average particle diameter, dispersibility and sphericity) of the polyester resin particles were measured and evaluated as follows. The results are shown in Tables 1 to 4.

[Particle States]

The average particle diameter and monodispersity of the particles were measured by using a laser diffraction type particle size distribution measurement apparatus (type SALD-2300 manufactured by Shimadzu Corporation, refractive index: 1.45-0.00i). The monodispersity was evaluated by a coefficient of variation obtained from the average particle diameter and a standard deviation.

The sphericity was evaluated by an average value (aspect ratio) of the ratios of long diameter to short diameter of the resin particles (50 particles) measured by imaging and analyzing pictures of the resin particles obtained by photographing under an electron microscope (JCM-5000 manufactured by JEOL, Ltd.).

Figure 2:
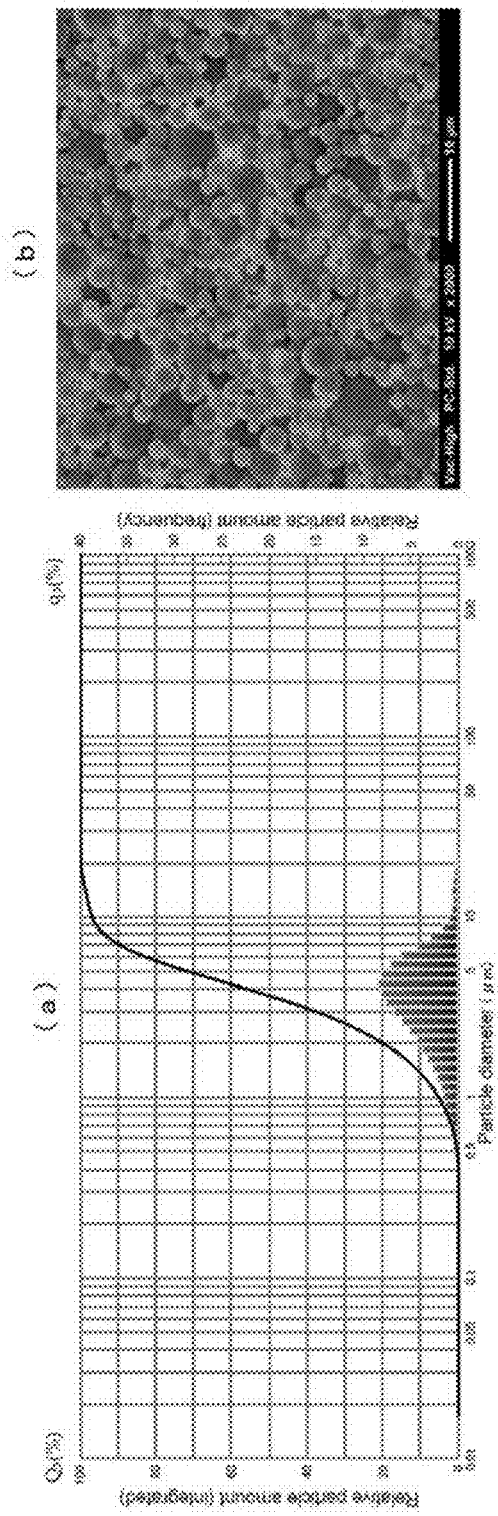
FIG. 2 shows the state of the particles in Comparative Example 1, wherein (a) is a measurement chart by a laser diffraction type particle size distribution measurement apparatus, and (b) is an electron microscope photograph.

FIGS. 1 and 2 show the particle states of Example 1 in comparison to those of Comparative Example 1, wherein (a) is a measurement chart by a laser diffraction type particle size distribution measurement apparatus, and (b) is an electron microscope photograph (magnification: 2,000 fold).

TABLE 1

| | | Examples | | | | | | |
|---|---|---|---|---|---|---|---|---|
| Items | | 1 | 2 | 3 | 4 | 5 | 6 | 7 |
| Polyester resin | A | | | | 40 | | | |
| | B | 40 | 40 | 40 | | 40 | 40 | 40 |
| | C | | | | | | | |
| | D | | | | | | | |
| Dispersing agent (A) | A | 0.08 | 0.08 | 0.08 | 0.08 | 0.18 | 0.08 | 0.09 |
| (Anionic polymer | B | | | | | | | |
| compound) | C | | | | | | | |
| | D | | | | | | | |
| Dispersing agent (B) | A | 1.92 | 1.92 | | 1.92 | 1.82 | | |
| (Polyvinyl alcohol) | B | | | 1.92 | | | | 7.91 |
| | C | | | | | | 3.92 | |
| Incorporation ratio of dispersing agents (A)/(B) | | 1/24 | 1/24 | 1/24 | 1/24 | 1/10 | 1/49 | 1/88 |
| Viscosity controlling | A | 0.1 | | 0.1 | 0.1 | 0.1 | 0.05 | 0.08 |
| agent | B | | | | | | | |
| Ethyl acetate | | 90 | 90 | 90 | 90 | 90 | 90 | 90 |
| Water | | 60 | 60 | 60 | 60 | 60 | 100 | 190 |
| Dispersing container | Impeller ratio | 0.66 | 0.66 | 0.65 | 0.63 | 0.63 | 0.65 | 0.72 |
| | Circumference velocity (m/s) | 4.1 | 4.1 | 7 | 1.5 | 3.6 | 2.3 | 2.3 |
| | Shape of impeller | A | A | A | B | A | A | A |
| Viscosity (Pa · s) | In dispersion step | 39.5 | 35.3 | 40.2 | 37.6 | 45.8 | 48.2 | 52.3 |
| | Aqueous dispersion | 0.9 | 0.1 | 0.8 | 1.1 | 1.1 | 1.2 | 2.0 |
| Stability | In dispersion step | ⊙ | ⊙ | ⊙ | ⊙ | ⊙ | ⊙ | ⊙ |
| | Aqueous dispersion | ⊙ | ○ | ⊙ | ⊙ | ⊙ | ⊙ | ⊙ |
| Particle form | Average particle diameter (μm) | 4.16 | 4.23 | 4.93 | 4.6 | 4.94 | 2.41 | 1.02 |
| | Standard deviation | 0.061 | 0.064 | 0.077 | 0.119 | 0.149 | 0.049 | 0.03 |
| Monodispersity | Coefficient of variation (%) | 1.47 | 1.52 | 1.56 | 2.59 | 3.02 | 2.02 | 2.91 |
| Sphericity | Aspect ratio | 1.04 | 1.04 | 1.05 | 1.04 | 1.05 | 1.03 | 1.02 |

TABLE 2

| | | Examples | | | | | | |
|---|---|---|---|---|---|---|---|---|
| Items | | 8 | 9 | 10 | 11 | 12 | 13 | 14 |
| Polyester resin | A | 40 | 40 | | | | 40 | |
| | B | | | 40 | 40 | 40 | | 40 |
| | C | | | | | | | |
| | D | | | | | | | |
| Dispersing agent (A) | A | 0.04 | | | 0.08 | 0.08 | 0.05 | |
| (Anionic polymer | B | | 0.08 | | | | | |
| compound) | C | | | 0.08 | | | | 0.16 |
| | D | | | | | | | |
| Dispersing agent (B) | A | 0.76 | 1.92 | | 1.92 | 1.92 | | 3.84 |
| (Polyvinyl alcohol) | B | | | 1.92 | | | | |
| | C | | | | | | 0.75 | |
| Incorporation ratio of dispersing agents (A)/(B) | | 1/19 | 1/24 | 1/24 | 1/24 | 1/24 | 1/15 | 1/24 |
| Viscosity controlling | A | 0.12 | | 0.1 | 0.06 | 0.12 | | 0.19 |
| agent | B | | 0.1 | | | | 0.04 | |
| Ethyl acetate | | 80 | 90 | 90 | 90 | 90 | 90 | 90 |
| Water | | 35 | 60 | 60 | 60 | 60 | 180 | 60 |
| Dispersing container | Impeller ratio | 0.63 | 0.63 | 0.66 | 0.8 | 0.5 | 0.63 | 0.66 |
| | Circumference velocity (m/s) | 5.5 | 5.5 | 4.1 | 3.2 | 4.5 | 5.5 | 4.1 |
| | Shape of impeller | B | A | A | A | B | B | A |

TABLE 2-continued

|  |  | Examples |  |  |  |  |  |  |
|---|---|---|---|---|---|---|---|---|
| Items |  | 8 | 9 | 10 | 11 | 12 | 13 | 14 |
| Viscosity (Pa · s) | In dispersion step | 19.3 | 24.3 | 46.8 | 41.1 | 35.3 | 3.2 | 58.7 |
|  | Aqueous dispersion | 3.6 | 0.8 | 1.0 | 0.9 | 0.9 | 0.2 | 4.8 |
| Stability | In dispersion step | ⊙ | ⊙ | ⊙ | ⊙ | ⊙ | ○ | ⊙ |
|  | Aqueous dispersion | ⊙ | ⊙ | ⊙ | ⊙ | ⊙ | ○ | ⊙ |
| Particle form | Average particle diameter (μm) | 8.86 | 8.45 | 3.89 | 4.22 | 4.89 | 20.3 | 2.57 |
|  | Standard deviation | 0.169 | 0.144 | 0.069 | 0.078 | 0.119 | 1.522 | 0.124 |
| Monodispersity | Coefficient of variation (%) | 1.91 | 2.23 | 1.77 | 1.85 | 2.43 | 7.5 | 4.83 |
| Sphericity | Aspect ratio | 1.06 | 1.05 | 1.05 | 1.04 | 1.08 | 1.08 | 1.03 |

TABLE 3

|  |  | Examples |  |  |  |  |  |  |
|---|---|---|---|---|---|---|---|---|
| Items |  | 15 | 16 | 17 | 18 | 19 | 20 | 21 |
| Polyester resin | A |  |  |  |  |  |  |  |
|  | B |  |  |  |  | 40 | 40 | 40 |
|  | C | 40 | 40 |  |  |  |  |  |
|  | D |  |  | 40 | 40 |  |  |  |
| Dispersing agent (A) (Anionic polymer compound) | A | 0.08 |  | 0.08 |  | 0.013 | 0.008 | 0.004 |
|  | B |  |  |  |  |  |  |  |
|  | C |  | 0.06 |  | 0.04 |  |  |  |
|  | D |  |  |  |  |  |  |  |
| Dispersing agent (B) (Polyvinyl alcohol) | A | 1.92 |  | 1.92 | 1.16 | 0.187 | 0.092 |  |
|  | B |  | 1.14 |  |  |  |  | 0.036 |
|  | C |  |  |  |  |  |  |  |
| Incorporation ratio of dispersing agents (A)/(B) |  | 1/24 | 1/19 | 1/24 | 1/29 | 1/14 | 1/11 | 1/10 |
| Viscosity controlling agent | A | 0.1 |  | 0.1 | 0.15 | 0.1 | 0.12 | 0.2 |
|  | B |  | 0.16 |  |  |  |  |  |
| Ethyl acetate |  | 90 | 100 | 90 | 110 | 80 | 90 | 90 |
| Water |  | 60 | 40 | 60 | 40 | 60 | 90 | 160 |
| Dispersing container | Impeller ratio | 0.66 | 0.72 | 0.66 | 0.72 | 0.66 | 0.63 | 0.63 |
|  | Circumference velocity (m/s) | 4.1 | 2.3 | 4.1 | 2.3 | 4.1 | 3.6 | 2.0 |
|  | Shape of impeller | A | B | A | B | A | A | B |
| Viscosity (Pa · s) | In dispersion step | 15.1 | 18.8 | 20.4 | 32.1 | 10.3 | 3.5 | 1.2 |
|  | Aqueous dispersion | 0.3 | 1.5 | 0.5 | 2.2 | 0.2 | 0.2 | 0.1 |
| Stability | In dispersion step | ⊙ | ⊙ | ⊙ | ⊙ | ⊙ | ⊙ | ⊙ |
|  | Aqueous dispersion | ⊙ | ⊙ | ⊙ | ⊙ | ○ | ○ | ○ |
| Particle form | Average particle diameter (μm) | 3.22 | 4.56 | 3.84 | 5.5 | 100.6 | 312.7 | 828.5 |
|  | Standard deviation | 0.206 | 0.244 | 0.131 | 0.142 | 2.233 | 9.1 | 48.3 |
| Monodispersity | Coefficient of variation (%) | 6.39 | 5.36 | 3.42 | 2.59 | 2.22 | 2.91 | 5.83 |
| Sphericity | Aspect ratio | 1.08 | 1.08 | 1.06 | 1.07 | 1.04 | 1.04 | 1.08 |

TABLE 4

|  |  | Comparative Examples |  |  |  |  |
|---|---|---|---|---|---|---|
| Items |  | 1 | 2 | 3 | 4 | 5 |
| Polyester resin | A |  |  |  | 40 | 40 |
|  | B | 40 | 40 | 40 |  |  |
|  | C |  |  |  |  |  |
|  | D |  |  |  |  |  |
| Dispersing agent (A) (Anionic polymer compound) | A | 0.48 | 0.48 | 0.01 |  | 0.08 |
|  | B |  |  |  |  |  |
|  | C |  |  |  |  |  |
|  | D |  |  |  | 0.08 |  |
| Dispersing agent (B) (Polyvinyl alcohol) | A | 1.12 | 1.12 | 1.99 | 1.92 | 0.12 |
|  | B |  |  |  |  |  |
|  | C |  |  |  |  |  |
| Incorporation ratio of dispersing agents (A)/(B) |  | 3/7 | 3/7 | 1/199 | 1/24 | 4/6 |
| Viscosity controlling agent | A |  | 0.08 | 0.08 | 0.1 | 0.15 |
|  | B |  |  |  |  |  |
| Ethyl acetate |  | 90 | 90 | 90 | 90 | 100 |
| Water |  | 60 | 60 | 60 | 60 | 200 |

TABLE 4-continued

|  | Items | Comparative Examples | | | | |
|---|---|---|---|---|---|---|
|  |  | 1 | 2 | 3 | 4 | 5 |
| Dispersing container | Impeller ratio | 0.9 | 0.66 | 0.66 | 0.63 | 0.66 |
|  | Circumference velocity (m/s) | 16 | 4.1 | 4.1 | 5.5 | 10 |
|  | Shape of impeller | C | A | A | B | A |
| Viscosity (Pa · s) | In dispersion step | 81.6 | 55.3 | 30.2 | 11.9 | 23.5 |
|  | Aqueous dispersion | 1.0 | 1.5 | — | 0.2 | 0.2 |
| Stability | In dispersion step | ⊙ | ○ | X | ○ | ○ |
|  | Aqueous dispersion | ⊙ | Δ | — | Δ | Δ |
| Particle form | Average particle diameter (μm) | 3.57 | 20.3 | N.D | 15.3 | 295.4 |
|  | Standard deviation | 0.309 | 3.289 |  | 1.561 | 37.5 |
| Monodispersity | Coefficiency of variation (%) | 8.65 | 16.2 |  | 10.2 | 12.7 |
| Sphericity | Aspect ratio | 1.05 | 1.09 |  | 1.08 | 1.08 |

It is understood from Tables 1 to 4 that Examples 1 to 21 of the present invention are excellent in sphericity, monodispersity and stability. On the other hand, it is understood that, in Comparative Examples 1 and 2, wherein the incorporation ratio of dispersing agents of (A)/(B) is out of the definition of the present invention, the coefficient of variation is more than 8 and the monodispersity is poor, and the same applies to Comparative Example 5. Furthermore, it is understood that stability is also poor in Comparative Example 2. In Comparative Example 3, it was difficult to disperse stably. It is understood that the monodispersity and stability are poor also in Comparative Example 4, wherein the average molecular weight of the anionic polymer compound of Dispersing agent (A) is out of the definition of the present invention.

Examples 22 and 23 and Comparative Examples 6 to 8

[Water Repellency (Sedimentability Test)]
For the resin particles of Examples 1 and 8 and Comparative Example 1, and the polylactic acid resin particles obtained by an extrusion molding method and a frost shattering method, 0.1 g of the resin particles was weighed and put on medical paper, the resin particles are gently put on a water surface of a 200 mL beaker containing 150 mL of ion exchanged water, and the state of the sedimentation of the resin particles was visually evaluated by the following criteria. The results are shown in Table 5.

Incidentally, the resin particles of the extrusion molding method used in Comparative Example 7 were polylactic acid particles obtained by mixing a polylactic acid resin and a polyethylene glycol having a number average molecular weight of 20,000 at a ratio of 1:1.5, putting the mixture into an extrusion molding machine and melt-kneading the mixture at 200° C., putting the melted resin into a water bath under stirring to give a suspension liquid of resin particles, and separating the resin particles by centrifugation. The particle states of the polylactic acid resin produced by the extrusion molding method were an average particle diameter of 5 μm, a coefficient of variation of 15% and an aspect ratio of 1.8, and the shapes were globular, and approximately globular including an oval globular shape, a comma-shape and a needle shape. Furthermore, the resin particles of the frost shattering method used in Comparative Example 8 were polylactic acid particles obtained by forming a polylactic acid resin into microparticles by a freeze shattering machine. The particle states of the polylactic acid resin produced by the frost shattering method were an average particle diameter of 5 μm, a coefficient of variation of 18% and an aspect ratio of 2.3, and the shape was such that the cross-sectional surface had a sharp rock shape or needle shape.

Evaluation Criteria

○: Sedimentation was not observed at the time when 24 hours had lapsed.

Δ: A part of the particles sedimented within 24 hours.

x: Half or more of the entirety sedimented immediately after the initiation of the test.

Incidentally, in the resin particles of Comparative Example 6, the dispersing agent and the viscosity controlling agent on the surfaces of the resin particles were detached from the surfaces, and the water repellant became fine (○), by further repeating the above-mentioned washing operations twice. In the resin particles of Comparative Example 7, the evaluation was not changed even the above-mentioned washing operations were repeated five times.

That is, it was recognized that complex operations can be decreased in the preparation of the spherical monodispersed polyester resin particles having water repellency of the present invention.

3. Cosmetic Product

[Loose Powder]
A loose powder was prepared by using each of the resin particles of Examples 1 and 8, Comparative Example 1, the extrusion molding method (Comparative Example 7) and the frost shattering method (Comparative Example 8), and a sensory test was conducted on feeling of use (texture, gloss, smoothness and makeup lasting).

The loose powder was prepared by incorporating 10% by mass of the resin particles, 68.7% by mass of mica, 10% by mass of titanium dioxide, 5% by mass of zinc oxide, and 6.3% by mass of coloring pigments (yellow iron oxide, red iron oxide, black iron oxide). A commercially available liquid foundation was applied to the back of the right hand of a subject, and the loose powder was applied onto the foundation. The respective items of feeling of use were evaluated by ten subjects by 1 to 5 points, and represented by average values. The results are shown in Table 5.

TABLE 5

|  | | Examples | | Comparative Examples | | |
| --- | --- | --- | --- | --- | --- | --- |
| Items | | 22 | 23 | 6 | 7 | 8 |
| Resin particles | | Example 1 | Example 8 | Comparative Example 1 | Extrusion molding method | Frost shattering method |
| Water repellency | | ○ | ○ | Δ | X | ○ |
| Sensory test | Texture | 4.5 | 4.0 | 4.2 | 2.4 | 1.8 |
| | Gloss | 4.8 | 4.6 | 3.8 | 3.5 | 3.0 |
| | Smoothness | 4.6 | 4.5 | 3.6 | 3.2 | 1.5 |
| | Makeup lasting | 4.8 | 4.4 | 3.0 | 2.3 | 3.8 |

[Powder Foundation]

A powder foundation was prepared by using the resin particles of Example 1. The powder foundation was prepared by incorporating 11% by mass of resin particles, 18% by mass of mica, 10% by mass of sericite, 28.5% by mass of talc, 15% by mass of titanium dioxide, 2% by mass of a silicone powder, 1.5% by mass of vaseline, 3% by mass of dimethycone, 1.5% by mass of isocetyl myristate, 2% by mass of 2-ethylhexylparamethoxycinnamate, 2% by mass of liquid paraffin and 5.5% by mass of coloring pigments (yellow iron oxide, red iron oxide, black iron oxide). The obtained compounded product had high transparency, and extremely fine adhesibility and extensibility to the skin.

[Eye Shadow]

An eye shadow was prepared by using the resin particles of Example 1. The eye shadow was prepared by incorporating 7% by mass of the resin particles, 38% by mass of mica, 20% by mass of a pearl agent, 5% by mass of talc, 5% by mass of titanium mica, 5% by mass of zinc stearate, 3% by mass of zinc laurate, 7% by mass of liquid paraffin, and 10% by mass of coloring pigments (yellow iron oxide, red iron oxide, black iron oxide). The obtained compounded product had extremely fine adhesibility and extensibility to the skin.

[Scrub Face-wash]

A scrub face-wash was prepared by using each of the resin particles of Examples 20 and 21, Comparative Example 5, the extrusion molding and the frost shattering method, and a sensory test was conducted on feeling of use (removal of smudge, rinsing property, and skin irritation).

Figure 3:
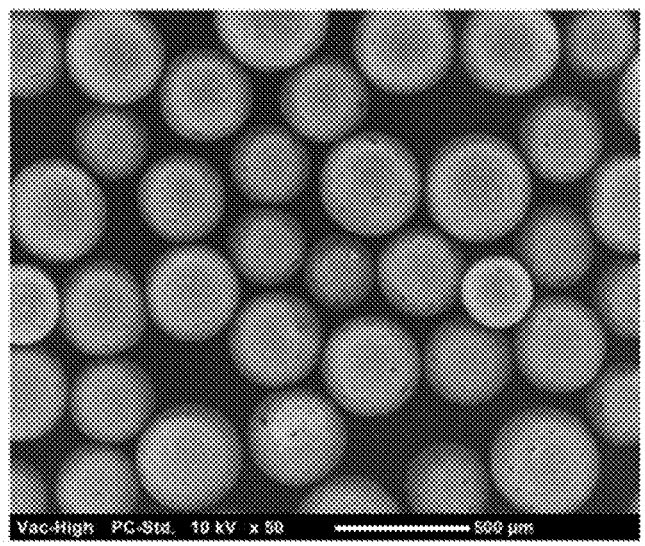
FIG. 3 shows an electron microscope photograph of the resin particles of Example 20.
Figure 4:
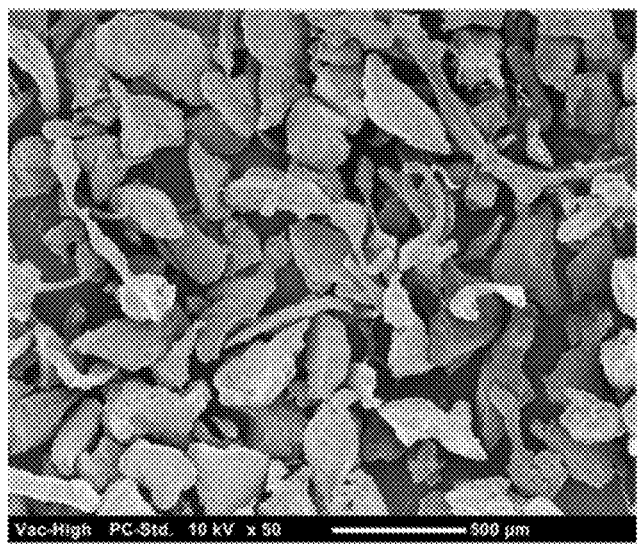
FIG. 4 shows an electron microscope photograph of the resin particles of Comparative Example 11 by a frost shattering method.

Incidentally, the resin particles of the extrusion molding method used in Comparative Example 10 were polylactic acid particles obtained by mixing a polylactic acid resin and a polyethylene glycol having a number average molecular weight of 20,000 at a ratio of 1:0.8, putting the mixture into an extrusion molding machine and melt-kneading the mixture at 200° C., putting the melted resin into a water bath under stirring to form a suspension liquid of the resin particles, and had an average particle diameter of 300 μm, a coefficient of variation of 12% and an aspect ratio of 1.6, and had an approximately globular shape, including an oval globular shape, a comma-shape and a needle shape. The resin particles of the frost shattering method used in Comparative Example 11 were polylactic acid particles obtained by forming a polylactic acid resin into microparticles in a freeze shattering machine, and the obtained resin particles had an average particle diameter of 300 μm and a coefficient of variation of 13% and a shape having a cross-sectional surface of a sharp rock shape or needle shape. FIGS. 3 and 4 show the particle states of Example 20 and Comparative Example 11 in comparison. FIG. 3 is an electron microscope photograph (magnification: 50-fold) of the resin particles of Example 20, and FIG. 4 is an electron microscope photograph (magnification: 50-fold) of the resin particles by the freeze shattering of Comparative Example 11.

A scrub face-wash was prepared by respectively incorporating 0.5% by mass of the resin particles, 11% by mass of potassium laurate, 6% by mass of potassium myristate, 2% by mass of potassium palmitate, 1% by mass of potassium stearate, 5% by mass of lauryl hydroxysultine, 5% by mass of a polyoxyethylene palm oil aliphatic acid, 10% by mass of glycerin, 0.2% by mass of tetrasodium edetate, suitable flavor materials, and purified water as a balance so that the whole amount became 100% by mass. A commercially available liquid foundation was applied onto the right cheek of a subject, and then washed away by using the prepared scrub face-wash. The respective items were evaluated by ten subjects by 1 to 5 points, and the average values thereof are shown. The results are shown in Table 6.

TABLE 6

|  | | Examples | | Comparative Examples | | |
| --- | --- | --- | --- | --- | --- | --- |
| Items | | 24 | 25 | 9 | 10 | 11 |
| Resin particles | | Example 20 | Example 21 | Comparative Example 5 | Extrusion molding method | Frost shattering method |
| Sensory test | Removal of smudge | 4.6 | 3.8 | 4.2 | 3.4 | 4.5 |
| | Rinsing property | 4.8 | 4.5 | 3.6 | 3.0 | 3.8 |
| | Skin irritation | 4.5 | 4.6 | 4.0 | 3.0 | 2.4 |

[Scrub Body Soap]

Scrub body soaps were prepared by using the resin particles of Example 20 and Comparative Example 5. Each scrub body soap was prepared by respectively incorporating 0.3% by mass of the resin particles, 10% by mass of potassium laurate, 3.5% by mass of potassium myristate, 1.5% by mass of potassium palmitate, 5% by mass of propylbetaine lauramide, 3% by mass of a polyoxyethylene palm glyceryl aliphatate, 5% by mass of glycerin and L-menthol, and suitable flavor materials, and purified water as a balance, so that the whole amount became 100% by mass. The scrub body soap prepared by using the resin particles of Example 20 had fine washing property, provide small irritation on the skin and extremely fine rinsing property as compared to the scrub body soap prepared by using the resin particles of Comparative Example 5, and provided smooth touch and feeling of use such that uncomfortable feeling is not provided to the skin.

[Scrub Hand Soap]

Scrub hand soaps were prepared by using the resin particles of Example 20 and Comparative Example 5. Each scrub hand soap was prepared by respectively incorporating by mass of the resin, particles, 10% by mass of a potassium palm oil aliphatate, 3% by mass of laurylhydroxysultine, 2% by mass of cocamidepropylbetaine, 3% by mass of a polyoxyethylene palm glyceryl aliphatate, 3% by mass of glycerin, 0.2% by mass of tetrasodium editate, a bactericide (triclosan), suitable flavor materials, and purified water as a balance so that the whole amount became 100% by mass. The scrub hand soap prepared by using the resin particles of Example 20 had fine washing property, provide small irritation on the skin and extremely fine rinsing property as compared to the scrub hand soap prepared by using the resin particles of Comparative Example 5, and provided smooth touch and feeling of use such that uncomfortable feeling is not provided to the skin.

As is apparent from above, it was recognized that the cosmetic products containing the spherical monodispersed polyester resin particles of the present invention are especially superior to the resin particle-containing cosmetic products of the extrusion molding method and the frost shattering method, and can provide finer feeling of use than that of a cosmetic product containing spherical polydispersed resin particles.

Accordingly, it was recognized that the spherical monodispersed polyester resin particles of the present invention can be utilized extremely usefully and practically in industries.

The invention claimed is:

1. A spherical monodispersed polyester resin aqueous dispersion, comprising a polyester resin dispersed in water,
    wherein the polyester resin has a particle average particle diameter in the range of from 1 to 1,000 µm, a sphericity in the range of from 1.00 to 1.10 as an average value (aspect ratio) of the long diameter/short diameter of the particles, and a monodispersity as a coefficient of variation from the average particle diameter and a standard deviation of 8% or less,
    the dispersion contains, together with the polyester resin,
    (A) an anionic polymer compound having an average molecular weight of 5,000,000 or more and 25,000,000 or less, and
    (B) a polyvinyl alcohol, as dispersing agents, at a ratio in the range of from 1/10 to 1/99 by mass ratio (A/B), and the dispersion has a viscosity in the range of from 0.1 to 5 Pa·s.

2. The spherical monodispersed polyester resin aqueous dispersion according to claim 1, wherein the total mass of the dispersing agents (A) and (B) is in the range of from 0.1 to 20% as a mass ratio with respect to the polyester resin.

3. The spherical monodispersed polyester resin aqueous dispersion according to claim 1, wherein the total mass of the dispersing agents (A) and (B) and the polyester resin is in the range of from 1/9 to 7/3 as a mass ratio with respect to the water.

4. The spherical monodispersed polyester resin aqueous dispersion according to claim 1, wherein the anionic polymer compound having an average molecular weight of 5,000,000 or more and 25,000,000 or less (A) as the dispersing agent is a polymer or copolymer containing at least one kind of unsaturated carboxylic acid-based monomers, unsaturated sulfonic acid-based monomers and neutralized products thereof.

5. The spherical monodispersed polyester resin aqueous dispersion according to claim 1, wherein the polyvinyl alcohol (B) as the dispersing agent has a saponification degree in the range of from 70 to 90%, and an average molecular weight in the range of from 50,000 to 300,000.

6. The spherical monodispersed polyester resin aqueous dispersion according to claim 1, wherein the dispersion contains a viscosity controlling agent.

7. A method for producing the spherical monodispersed polyester resin aqueous dispersion according to claim 1, comprising mixing a polyester resin, and the dispersing agents (A) and (B), or the dispersing agents (A) and (B) and a viscosity controlling agent, with water and an organic solvent, by means of stirring.

8. The method for producing the spherical monodispersed polyester resin aqueous dispersion according to claim 7, wherein the viscosity after heat dispersion and cooling during the mixing by means of stirring is set to be in the range of from 1.0 to 60 Pa·s.

9. The method for producing the spherical monodispersed polyester resin aqueous dispersion according to claim 7, wherein the mixing by means of stirring is conducted by a rotary stirrer having an impeller, and a ratio ($d_1/d_2$) of an impeller diameter ($d_1$) of the impeller to an inner diameter of a stirring container ($d_2$) during the mixing is set to be in the range of from 0.5 to 0.85, and the circumference velocity of the impeller is set to be 1 to 8 m/s.

10. A method for producing a spherical monodispersed polyester resin particle, the method comprising separating resin particles from the spherical monodispersed polyester resin aqueous dispersion according to claim 1, and washing and drying the resin particles.

11. A method for producing a cosmetic product, the method comprising:
    producing the spherical monodispersed polyester resin particles according to claim 10; and
    using the spherical monodispersed polyester resin particles as an additive for cosmetic products.

* * * * *